(12) United States Patent
Bury et al.

(10) Patent No.: US 8,680,265 B2
(45) Date of Patent: Mar. 25, 2014

(54) PROCESS FOR THE PREPARATION OF A BORON-SUBSTITUTED PORPHYRIN

(75) Inventors: Paul Stanley Bury, Bishop's Stortford (GB); Ke-Dong Li, Manchester (GB); Anthony David Bentham, Accrington (GB); Bipin Chandra Muljibhai Patel, Guildford (GB)

(73) Assignee: PSIMEI Pharmaceuticals (GB)

( * ) Notice: Subject to any disclaimer, the term of this patent is extended or adjusted under 35 U.S.C. 154(b) by 889 days.

(21) Appl. No.: 11/721,865

(22) PCT Filed: Dec. 13, 2005

(86) PCT No.: PCT/GB2005/004784
§ 371 (c)(1),
(2), (4) Date: Oct. 7, 2009

(87) PCT Pub. No.: WO2006/064205
PCT Pub. Date: Jun. 22, 2006

(65) Prior Publication Data
US 2010/0016613 A1    Jan. 21, 2010

(30) Foreign Application Priority Data
Dec. 16, 2004    (GB) .................................. 0427589.7

(51) Int. Cl.
*C07D 487/22* (2006.01)
*C07F 5/02* (2006.01)

(52) U.S. Cl.
USPC .................................. 540/145; 568/3; 568/5

(58) Field of Classification Search
USPC .......................................... 540/145; 568/3, 5
See application file for complete search history.

(56) References Cited

U.S. PATENT DOCUMENTS 5,877,165 A * 3/1999 Miura et al. .................... 514/64

FOREIGN PATENT DOCUMENTS

WO    WO 02/098417        12/2002
WO    WO 02/098417 A1 *  12/2002  ........... A61K 31/409
WO    WO 2006/088476 A2    8/2006

OTHER PUBLICATIONS

Miura et al. "Synthesis of copper octamotetracarboranylphenylporphyrin for boron neutron capture therapy and its toxicity and biodistribution in tumour-bearing mice" British Journal of Radiology, 2004, vol. 77, 573-580.*

Miura et al. "Preparation of Carboranyl Porphyrins for Boron Neutron Capture Therapy" Tetrahedron Letters, 1990, vol. 31, pp. 2247-2250.*
Lindsey et al. "Rothemund and Adler-Longo reactions revisited: synthesis of tetraphenylporphyrins under equilibrium conditions" Journal of Organic Chemistry, 1987, vol. 52, pp. 827-836.*
Miura, et al., *British Journal of Radiology*, 71(847):773-781, 1998.
Miura, et al., *British Journal of Radiology*, 77:573-580, 2004.
Miura, et al., *International Journal of Cancer*, 68(1):114-119, 1996.
Miura, et al., *Journal of Neuro-Oncology*, 52:111-117, 2001.
Miura, et al., *Radiation Research*, 155:603-610, 2001.
Miura, et al., *Tetrahedron Letters*, 31:2247-2250, 1990.
Soloway, et al., *Chem. Rev.*, 98:1515-1562, 1998.
Zakharkin, et al., *Russian Chemical Bulletin*, 48(12):2312-2314, 1999.
International Preliminary Report on Patentability, PCT/GB2005/004784, mailed on Jun. 13, 2007.

* cited by examiner

*Primary Examiner* — Joseph Kosack
(74) *Attorney, Agent, or Firm* — Choate, Hall & Stewart, LLP; Charles E. Lyon; Kristen C. Buteau

(57) ABSTRACT

Processes are disclosed for the preparation of a compound having the formula: (I) and intermediate compounds wherein M is a single-photon-emission tomography imageable radiometal and/or a paramagnetic metal, R is hydrogen or a halogen provided that at least one R is halogen and Y is selected from ortho, meta or para $O(CH_2)_n C_2 HB_9 H_{10}$ or $O(CH_2)_n C_2 HB_{10} H_{10}$ wherein n is 0 or an integer from 1 to 20 and $O(CH_2)_n C_2 HB_9 H_{10}$ is nido ortho-, meta- or para-carborane and $O(CH_2)_n C_2 HB_{10} H_{10}$ is ortho-, meta- or para-carborane.

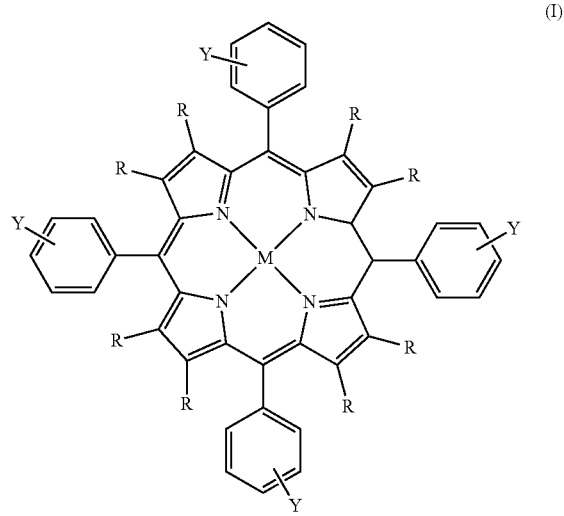

(I)

13 Claims, 1 Drawing Sheet

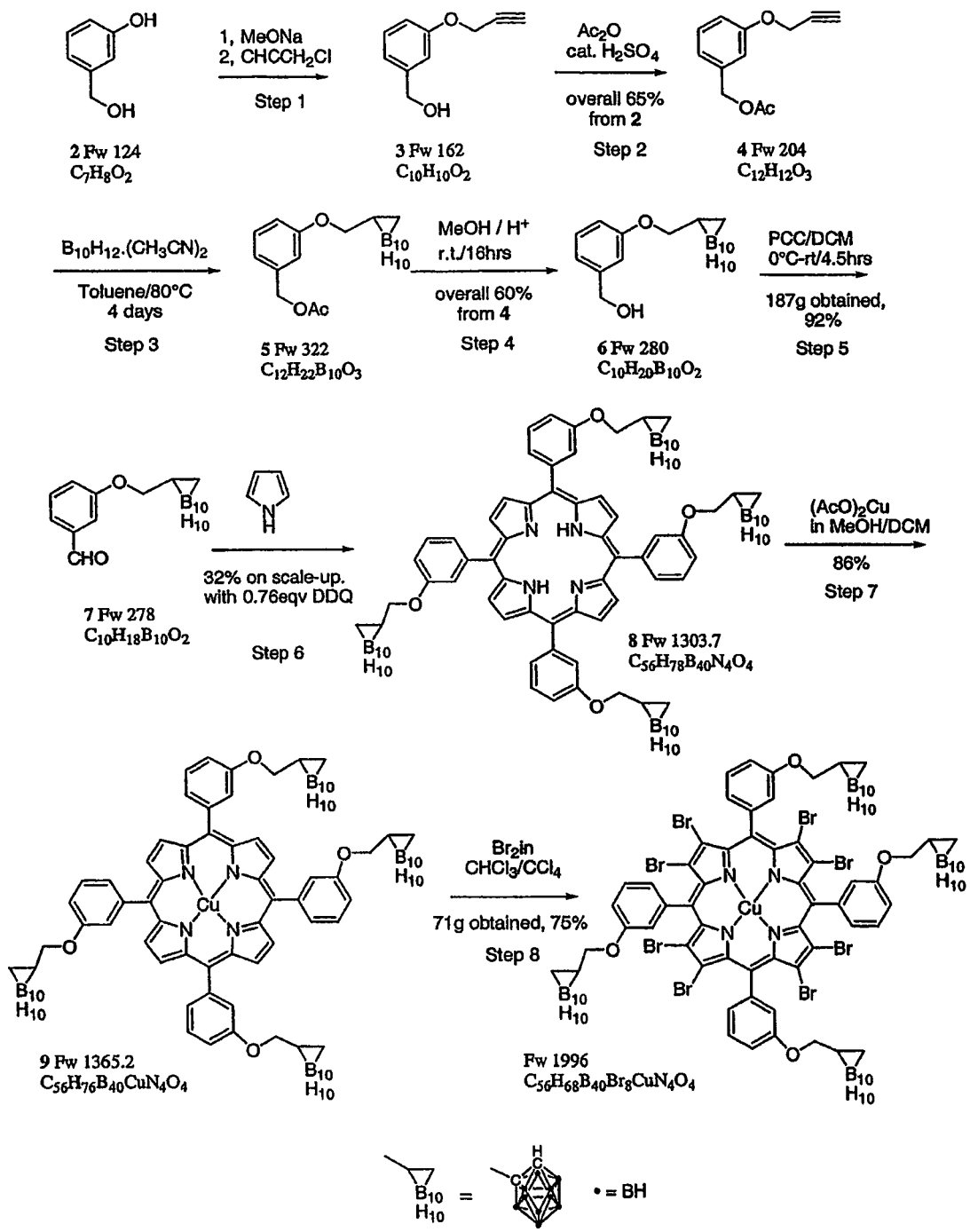

PROCESS FOR THE PREPARATION OF A BORON-SUBSTITUTED PORPHYRIN

The present application claims priority under 35 U.S.C. 371 to International Application No. PCT/GB2005/004784 (published PCT application No. WO 2006/064205), filed Dec. 13, 2005, which claims priority to Great Britain Application No. GB 0427589.7, filed Dec. 16, 2004. The entire contents of each of the above-referenced applications are incorporated herein by reference.

The present invention relates to a process for the production of a porphyrin of formula (I) and further to a process for the production of an intermediate compound such as compounds of formula (II).

Radiotherapy, although widely used in the management and the treatment of early to advanced stage cancers, has many drawbacks including normal tissue damage and burdensome treatment schedules (up to 6 weeks). Clinical radiotherapy and chemotherapy deliver survival rates that remain inadequate and in some instances totally unacceptable. However, where there is no alternative treatment, which is the case for the vast majority of cancer patients, the use of radiotherapeutic modalities prevails. It is projected that current research efforts will improve the delivery and the outcome of radiotherapy by only 10% over the next 10 years. That is, an increase from 30% to 33% cure rate, with the remaining balance of treatment achieving 70% palliation. A major challenge is to significantly improve this cure rate without compromising normal tissue tolerance. Conservative estimates suggest that over 100,000 patients are treated per day worldwide with conventional radiotherapy and over 5,000 new patients per day arrive into the treatment modality. There is clearly a need to improve the conventional radiotherapy methodology to provide improved cure rates.

One approach to improving cure rates is X-ray activated-drug therapy or photo activated drug therapy (PAT). In this method, an activatable drug is administered to the patient, and the drug is preferentially localised to tumour tissue. This approach may be combined with a number of standard radiotherapy techniques.

X-ray activated-drug therapy (PAT) is capable of replacing conventional radiotherapy for the treatment of cancer. Translation of x-ray activated-drug therapy into the clinic has the potential to deliver staggering cure rates of 85%, up from 30% with conventional radiotherapy.

Radiotherapy may be given using large X-ray machines. Occasionally gamma rays or electrons may be used. The activatable drugs can be activated using X-rays (as well as ionizing radiation such as gamma rays, electrons, protons, neutrons) that are used in conventional radiotherapy and its variants such as confocal radiotherapy, intensity modulated radiotherapy (IMRT), invasive internal radiotherapy and brachytherapy.

External X-rays are targeted by way of masks (contoured to the shape of the tumour) and beamed in from the outside. Single or multiple x-ray beams at different angles may be used to maximise the x-ray dose to tumour and concurrently minimise the x-ray dose to normal tissue.

Invasive internal radiotherapy involves the introduction of radioactive tubes into the tumour to give a very intense x-ray dose. A number of tumours can be treated in this way, in particular cancer of the cervix, breast and skin.

In brachytherapy, radioactive "seeds" are seriotactically placed within a tumour mass. The radioactive source is generally one of the following: Radium-226, Caesium-137, Cobalt-60, Iridium-192, Gold-198, Strontium-90, Yttrium-90. Other radionuclides suitable for unsealed use are Iodine-131, Phosphorous-32, Yttrium-90.

IMRT is a recent development which uses three dimensional data derived from magnetic resonance imaging (MRI), positron emission tomography (PET), single-photon-emission tomography (SPECT) and computed tomography (CT)-scans to deliver very precisely x-rays to the target. A pencil beam of x-rays is scanned over the tumour. The beam intensity and the duration (dwell-time) at any one point is varied to dump a maximum of x-ray energy for maximum cell kill. Total X-ray doses over 90-100 Gy are now being delivered and are proving to be highly successful.

However, IMRT is data hungry and requires information on the exact dimensions of a tumour and its spread, and small movements of the tumour (0.1 mm-1 mm) that arise from breathing and the heart beat result in less than optimal x-ray dose delivery to guerrilla cells at the edges of the tumour. Such cells escape treatment and can result in tumour recurrence. A real-time feedback to compensate for tumour movement would assist in this method.

Once a patient is diagnosed with cancer and a decision has been taken to treat the cancer with radiotherapy, patients undergo treatment planning and patient specific X-ray dose calculations generated from the exact location of the tumour, tumour spread and dimensions. Treatment planning information is derived from conventional diagnostic imaging techniques such as MRI, PET, SPECT as well X-ray images and CT scans. Careful planning is necessary to ensure that the treatment area and field includes all of the cancer and avoids vital organs (e.g. heart, spinal cord, gut). Improved methods of imagining tumours are required to assist in such planning.

Porphyrins have been applied in the prior art to various radiation type therapies including boron neutron capture therapy (BNCT) and photodynamic therapy (PDT). Porphyrins are known to have a high affinity for neoblastic tissues in mammals, including man (see, for example, Solloway et al, Chem Rev (1998), 98, 1515-1562, U.S. Pat. No. 5,877,165; British Journal of Radiology (1998), 71, 773-781; Journal of Neuro-Oncology (2001), 52, 111-117; and International Journal of Cancer (1996), 68, 114-119).

Of particular interest has been the category of porphyrins including synthetic tetraphenyl porphyrins (TPP) derivatives including CuTCPH and NiTCPH. These porphyrin rings, existing as chelating agents for nickel and copper atoms, exhibit very favourable localization to tumor tissue in preference to normal tissue or blood. For example, in U.S. Pat. No. 5,877,165 a tumor colon blood ratio of 16:1 is described.

There is a need for further and improved porphyrins for use in therapeutic and diagnostic methods. There is also a need for improved methods of manufacturing such porphyrins. The invention addresses these and other problems.

SUMMARY OF THE INVENTION

Accordingly, in a first aspect, the invention provides a process for the preparation of a compound having the formula I:

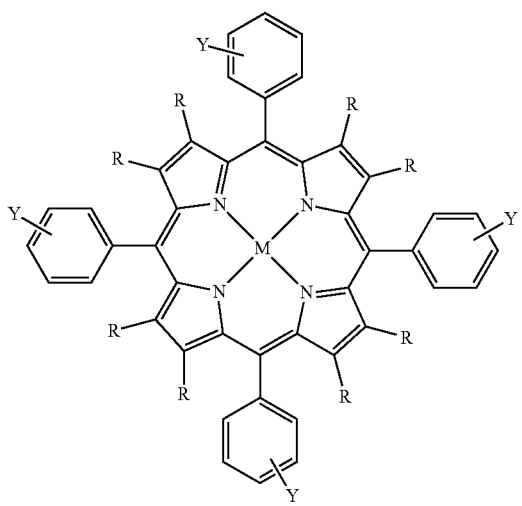

I wherein M is a single-photon-emission tomography imageable radiometal and/or a paramagnetic metal, R is hydrogen or a halogen provided that at least one R is halogen and Y is selected from ortho, meta or para $O(CH_2)_nC_2HB_9H_{10}$ or $O(CH_2)_nC_2HB_{10}H_{10}$ wherein n is 0 or an integer from 1 to 20 and $O(CH_2)_nC_2HB_9H_{10}$ is nido ortho-, meta- or para-carborane and $O(CH_2)_nC_2HB_{10}H_{10}$ is ortho-, meta- or para-carborane, said process comprising halogenating a compound having the formula III

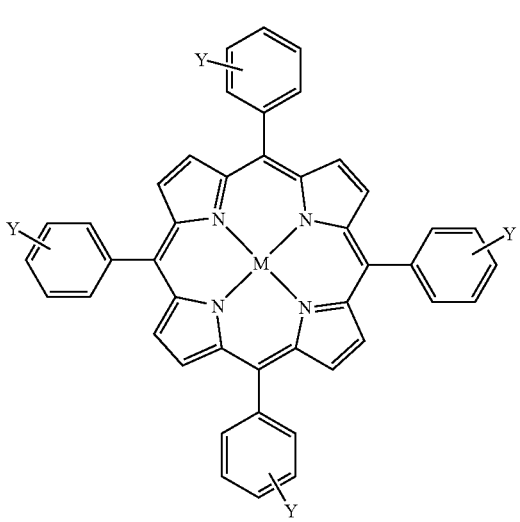

III wherein Y and M are as defined for the compound of formula I.

The compound of formula I produced by the process of the first aspect contains eight R groups. For the purposes of the invention, each R group is preferably halogen, more preferably each R group is bromide. Y is preferably selected from meta $O—(CH_2)_n—C_2HB_9H_{10}$ or meta $O—(CH_2)_n—C_2HB_{10}H_{10}$ wherein n is 0, 1, 2, 3, 4, 5, 6, 7, 8, 9 or 10. M is preferably a transition metal or a lanthanide metal.

In a particular feature of the first aspect of the invention, the process is preferably is a process for the formation of a compound of formula I wherein M is Cu, each R is bromide and Y is meta $O—CH_2—C_2HB_{10}H_{10}$.

The second aspect of the invention provides a process for the production of a compound of formula (III) as defined above said process comprising combining a compound having the formula II wherein Y is as defined for the compound of formula I;

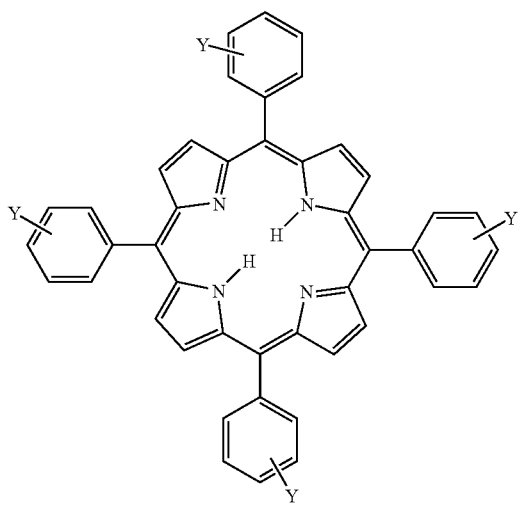

II with the acetate of the metal M

The third aspect of the invention provides a process for the production of a compound of formula I from a compound of formula II comprising combining a compound of formula II with a metal acetate to form a compound of formula III in situ, and then combining said in situ generated compound of formula III with a halogenating agent to form a compound of formula I. It will be appreciated that this one-pot synthesis allows the generation of a compound of formula III in situ and avoids the needs for isolation and purification of this intermediate compound.

For the purposes of this aspect of the invention, the compound of formula II is preferably combined with the metal acetate in dichloromethane. More preferably, the metal acetate is copper acetate. Halogenation of the in situ generated compound of formula III is preferably carried out with bromine. Halogenation preferably occurs in an aliphatic alcohol having from 1 to 6 carbon atoms, more preferably methanol.

The fourth aspect of the invention is directed to a process for the preparation of a compound having the formula II as defined above said process comprising a) combining an aldehyde having the formula

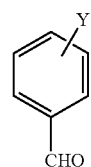

with pyrrole in the presence of a Lewis acid catalyst to form a compound having the formula IV

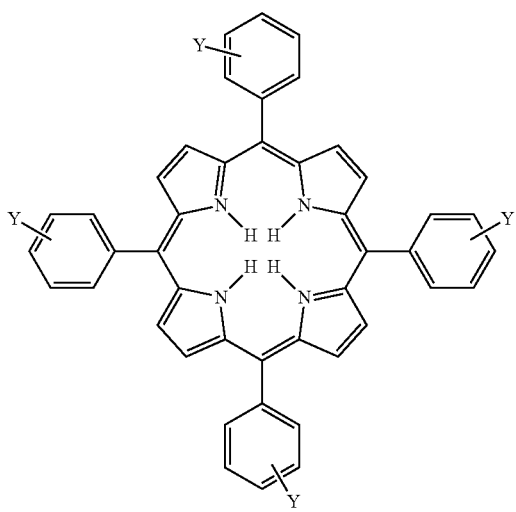

IV and;
b) oxidising the compound having the formula IV by the addition of from 0.01 to 2 molar equivalents 2,3-dicyanobenzoquinone based on the aldehyde.

The invention further relates to a process of producing a compound having the formula IV as set out above, said process comprising the process set out in step a) above. The invention further relates to a process for producing a compound of formula II from a compound of formula V via the process set out in step b) above.

The fifth aspect of the invention is directed to a process for the preparation of a compound having the formula I as defined above said process comprising
a) combining an aldehyde having the formula

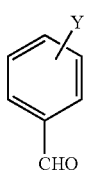

CHO with pyrrole in the presence of a Lewis acid catalyst to form a compound having the formula IV as defined above;
oxidising the compound having the formula IV by the addition of from 0.01 to 2 molar equivalents 2,3 dichloro-5,6 dicyanobenzoquinone based on the aldehyde to form a compound having the formula II as defined above;
c) combining a compound having the formula II with the acetate of the metal M to form a compound having the formula III as defined above; and,
d) combining the compound having the formula DI with a halogenating agent to form a compound having the formula I.

For the purposes of this aspect of the invention, the compound of formula II is preferably combined with the acetate of the metal M in a mixture of dichloromethane and methanol. Alternatively, the compound of formula II is preferably combined with the acetate of the metal M in dichloromethane. The reaction of the compound of formula II with the metal acetate preferably occurs at ambient temperature.

The halogenation preferably occurs in a mixed solvent solution, preferably a chlorinated solvent or a mixture of chlorinated solvents said chlorinated solvent being selected from trichloromethane, carbon tetrachloride and/or dichloromethane, more preferably dichloromethane. Alternatively, the halogenation is preferably carried out in an aliphatic alcohol having from 1 to 6 carbon atoms, preferably methanol. The halogenation preferably occurs at ambient temperature, The sixth aspect of the invention is directed to a further process for the preparation of a compound having the formula I as defined above said process comprising
a) combining an aldehyde having the formula

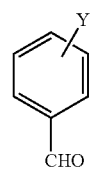

CHO with pyrrole in the presence of a Lewis acid catalyst to form a compound having the formula IV as defined above;
oxidising the compound having the formula IV by the addition of from 0.01 to 2 molar equivalents 2,3 dichloro-5,6 dicyanobenzoquinone based on the aldehyde to form a compound having the formula II as defined above;
c) combining a compound having the formula II with the acetate of the metal M to form a compound having the formula III in situ as defined above; and,
d) combining the compound having the formula III with a halogenating agent, to form a compound having the formula I.

The compound of formula II is produced in situ and is used directly in step d with no further isolation or purification. This process therefore provides a efficient method of synthesising a compound of formula I, while minimising the laborious and time consuming isolation and purification steps.

For the purposes of the sixth aspect of the invention, the compound having the formula (II) is preferably combined with the metal acetate in dichloromethane. Furthermore, the halogenation is preferably carried out in an aliphatic alcohol having 1 to 6 carbon atoms, preferably methanol. The insertion of the metal and the halogenation are preferably carried out at ambient temperature.

Each process described above provides for the reproducible production of enhanced levels e.g. tens of grams of the product of the process thereby allowing for scale up of the reaction in a way not previously possible and particularly allowing for the production of the products on a commercial scale.

The seventh aspect of the invention relates to a process for the formation of an aldehyde having the formula

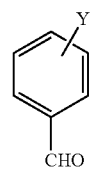

CHO wherein Y is as defined for a compound of formula I, comprising activation of a carborane with acetonitrile, reaction with propargyl oxybenzyl acetate to form an alcohol and subsequent oxidation. Preferably the carborane is decaborane.

For the avoidance of doubt, the groups R, M and Y in any of compounds of formula II, III, IV or the aldehyde are defined as for a compound of formula I. Furthermore, it will be appreciated that one or more of the processes set out for the present invention can be combined with one or more of the other process set out for the present invention to provide a process for the provision of compounds of formula I, II, III or IV as defined herein.

BRIEF DESCRIPTION OF THE FIGURES

FIG. 1 shows a reaction scheme for the preparation of the substituted porphyrin 1,2,3,4,5,6,7,8-octabromo-α,β,γ,δ-tetra-[3-(1,2-dicarbododecaborane-(12)-1-yl-methoxyl)phenyl]porphynato-copper$^{II}$ (also known as CuTCPBr).

DETAILED DESCRIPTION OF THE INVENTION

A process for the preparation of a compound having the formula I as defined comprises halogenation of a compound of formula III as defined above.

The compound having the formula III is combined with a halogenating agent in a solvent solution preferably comprising an aliphatic alcohol having from 1 to 6 carbon atoms, dichloromethane, trichloromethane and/or carbon tetrachloride or, preferably a mixed solvent system such as mixture of two or more of an aliphatic alcohol having from 1 to 6 carbon atoms, dichloromethane trichloromethane, and/or carbon tetrachloride. The mixed solvent is preferably trichloromethane and carbon tetrachloride. In a particular feature of the invention, the solvent system preferably comprises dichloromethane.

The solvent system may additionally comprise a base such as an organic base. Examples of suitable bases include pyridine, alcohols etc.

Where the compound of formula III is combined with a halogenating agent in an aliphatic alcohol, the aliphatic alcohol has from 1 to 6 carbon atoms, preferably 1 to 4 carbons atoms. The aliphatic alcohol can be one or more of methanol, ethanol, propanol, butanol, pentanol or hexanol. Preferably the aliphatic alcohol is methanol. It will be appreciated that when the halogenation is carried out in an aliphatic alcohol, it is not necessary to use an organic base such as pyridine.

The halogen represented by R may be F, Cl, Br, I, preferably Br.

Examples of suitable halogenating agents are $F_2$, $Cl_2$, $Br_2$ and $I_2$. A particularly preferred halogenating agent is bromine.

As discussed above, for a compound of formula I, one or more of the groups R is a halogen, preferably two, three, four, five, six, seven or eight of the groups R are halogen, most preferably all the R groups are halogen. The halogenating agent will therefore be provided in sufficient quantity to allow the desired degree of halogenation. Preferably, sufficient halogenating agent is used to ensure that each R in formula I represents halogen. The halogenating agent will therefore be provided in sufficient excess to ensure that each R in formula I represents halogen. The halogenating agent can be provided at a level of 8 to 20 equivalents (compared to the amount of the compound of formula III), preferably at a level of 9 to 14 equivalents.

Preferably, a solution of the halogenating agent is added incrementally to a solution of the compound of formula III over a period from 1 minute to 6 hrs, preferably from 0.5 hr to 3 hours and the resulting mixture stirred for a period from 10 minutes to 6 hours, preferably 1 hour to 4 hours.

The reaction may be carried out at a temperature from 0 to 80° C., preferably at ambient temperature.

Preferably, a base such as pyridine is added and the resulting mixture stirred for a period from 2 hours to 48 hours.

Where the compound of formula I is formed by combining a compound of formula If with a halogenating agent and an aliphatic alcohol having from 1 to 6 carbon atoms, the halogenating agent is preferably bromine.

It will be appreciated that any remaining halogenating agent or any reaction products of the halogenating agent should be removed from the reaction mixture after the halogenation step has been completed. This removal can be carried out using methods well known in the art. In a preferred feature of the invention, hydrogen bromide, formed during the formation of a compound of formula I, is removed using a base, preferably an inorganic base, such as one or more bicarbonate salts of a group 1A metal.

The compound of the formula III is produced by combining a compound having the formula II as defined above with the acetate of the metal M, preferably at ambient temperature, to form a compound having the formula III.

For the purposes of this invention, the metal M may be selected from the transition metals or the lanthanide metals such as vanadium (V), chromium (Cr), manganese (Mn), iron (Fe), ruthenium (Ru), technetium (Tc), chromium (Cr), platinum (Pt), lead (Pd), cobalt (Co), cadmium (Cd), nickel (Ni), copper (Cu), zinc (Zn), germanium (Ge), molybdenum (Mo), indium (In), tin (Sn), yttrium (Y), gold (Au), barium (Ba), tungsten (W), and gadolinium (Gd). The most preferred metals are Cu, Zn, Ni, Pb and Mn.

The metal acetate is preferably provided at a level of 1 to 5 equivalents (compared to the amount of compound of formula II), more preferably at a level of from 1.1 to 1.5 equivalents.

The formation of a compound of formula III is preferably carried out in a mixture of dichloromethane and methanol. The molar ratio of dichloromethane and methanol in the solvent mixture may be from 10:1 to 1:5. Alternatively, the formation of a compound of formula III can be carried out in dichloromethane. Where the compound of formula III is produced by the combination of a compound of formula II with a metal acetate in dichloromethane, the metal acetate is preferably copper acetate.

The reaction may be carried out at a temperature from 10 to 70° C., more preferably at a temperature from 15 to 60° C., more preferably at ambient temperature.

The reaction may be carried out for a period of time from 0.01 hour to 2 hours, preferably from 0.1 hour to 0.5 hour.

The compound having the formula II as defined above may be prepared by a process comprising combining an aldehyde having the formula

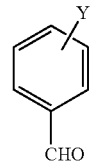

wherein Y is as defined above with pyrrole in the presence of a Lewis acid catalyst to form a compound having the formula IV as defined above.

The use of pure pyrrole, preferably freshly distilled pyrrole, enhances the yield. The pyrrole is preferably at least 98% to 99.99% pure, more preferably from 99.5% to 99.99% pure.

Preferred solvents for the reaction include dichloromethane (DCM) and trichloromethane.

Suitable Lewis acid catalysts include but are not limited to trifluoroacetic acid, $ZnCl_2$, $FeCl_2$, $FeCl_3$, $AlBr_3$, $AlCl_3$, $H_2SO_4$, $HNO_3$. A preferred Lewis acid catalyst is boron trifluoride diethyl etherate.

The reaction is preferably carried out in the absence of oxygen. Preferably, a stream of dry nitrogen is passed through a mixture of the aldehyde and pyrrole in the solvent to remove all traces of oxygen before addition of the Lewis acid catalyst.

The reaction mixture may be stirred for a period of time from 5 minutes to 6 hours, preferably about 1.5 hr. The reaction is preferably carried out at ambient temperature.

Furthermore, the reaction is preferably anhydrous. Preferably, all traces of water are removed e.g. by the addition of activated molecular sieves and the resulting solution stirred for a period of time from 5 minutes to 3 hours and/or the drying of solvents, reagents and glassware before use.

The reaction mixture may then be treated with from 0.01 to 2, preferably from 0.1 to 1 molar equivalents 2,3-dichloro-5,6-dicyanobenzoquinone (DDQ) based on the aldehyde. It may be preferred to use less than 1 molar equivalent DDQ based on the aldehyde. Such quantities were found to improve the yield of compound II. The resulting solution is preferably stirred for a period of time from 2 hours to 72 hours, preferably at ambient temperature. The aldehyde having the formula

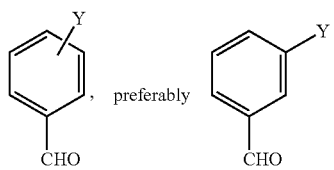

used in the preparation of the compound having the formula II as defined above may be prepared in several stages following the procedure described in Miura, M., et al, "Preparation of Carboranyl Porphyrins for Boron Neutron Capture Therapy", Tetrahedron Letters, 31, 2247-2250, (1990) for the purposes of this invention, Y is preferably $O—CH_2—C_2HB_{10}H_{10}$.

Alternatively the aldehyde can be produced by one or more higher yielding processes as described in the examples.

The invention further relates to the products of the processes set out above. In particular, the invention relates to a compound of formula I, II, I or V or an aldehyde as described herein as produced according to one or more of the processes set out in the invention. The compounds of the invention, particularly compounds of formula I can be used in the treatment of cancer, in particular in X-ray activated-drug therapy or photo activated drug therapy.

All preferred features of each of the aspects of the invention apply to all others mutatis mutandis.

The invention is described by way of one or more of the non-limiting examples as follows:

Example 1

All reactions were carried out under a nitrogen atmosphere in high temperature oven-dried glassware, with magnetic stirring or overhead stirrer unless otherwise stated. All intermediates and products were identified by means of proton NMR (where possible), TLC and MALDI TOF mass spectroscopy (in a dithranol matrix).

Preparation of 3-propargyloxybenzyl alcohol 3

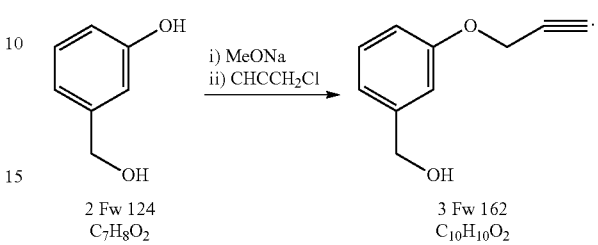

A 20.0 L flange flask was charged with 3-hydroxybenzyl alcohol (97%, ex. Aldrich, 903 g, 7.28 mol, 1 eq.) in methanol (MeOH)(9.1 L, dried over 3 A molecular sieves) to give a clear solution, into which sodium methoxide (25% in methanol, ex. Aldrich, 1.746 L, 7.63 mol, 1.05 eq.) was slowly added with vigorous stirring. After stirring for 10 min. the propargyl chloride (70 wt % in toluene, ex. Aldrich, 542.6 g, 805 ml, 7.29 mol, 1 eq) was added slowly with vigorous stirring over a period of 30 minutes. The reaction mixture was heated under reflux for 40 h (isomantle set to 76° C. with an internal temp. of 64° C.). TLC-examination (10% MeOH in DCM) showed that the reaction was not complete. The reaction was nevertheless worked-up at this stage. The MeOH was removed by rotary evaporation, and the residue dissolved in DCM (10.2 L) to give a clear solution, which was washed with water (5.82 L×3), and dried over sodium sulfate. The solvent was removed in vacuo, to give the title compound (706 g, 60%) as an orange gum.

Preparation of 3-propargyloxybenzyl acetate 4

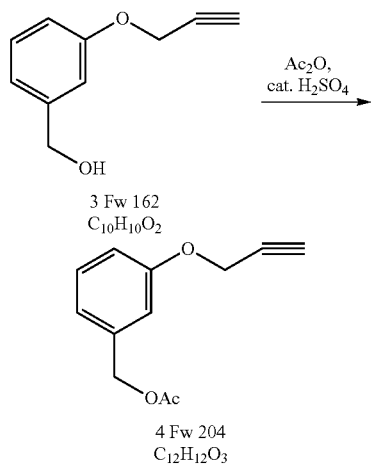

The starting material for this step was the crude material described above, containing the propargyloxy material 3 and some of the hydroxybenzyl alcohol 2.

A 5.0 L flange flask was charged with 3 (706 g, approx. 4.36 mol, 1 eq) and acetic anhydride (99.5%, ex. Fisher, 1300 ml, 1 mol) to give a clear solution. Sulfuric acid (conc. 98%, 150 drops, ~3 ml, catalytic) was then added very slowly (dropwise) over 30 minutes, with cooling to 0° C. by aid of an ice/water bath to control the exotherm to give a very dark reaction mixture. Maximum internal temperature observed was 45° C. After the addition the reaction mixture was stirred for 30 min, then the reaction mixture was stirred at 99° C. for 3 h. TLC-examination (silica-gel plate, DCM eluent, PMA stain) showed that all the starting material had been consumed. The mixture was cooled to room temperature (r.t.) overnight to give a dark green solution, which was poured onto an ice-water mixture (2.5 L water and 2.5 Kg of ice) with vigorous stirring. The product was extracted with DCM (5.0 L×3), and the combined extracts washed with water (3.0 L×3), dried over $Na_2SO_4$, and evaporated to give a black/brown oily residue.

The crude product was purified by vacuum distillation to give the title compound 4 (598 g, 67%; 40% combined yield for both steps from 2) as a colourless oil; bp.=92-80° C./0.1-0.05 mmHg (oil-bath 127-140° C.).

A compound of formula (4) can be prepared by the improved procedure documented below. This alternative procedure allows the production of (4) and subsequent compounds derived therefrom in a higher yield and a more cost effective manner.

1) Acetylation with Propargyl Bromide

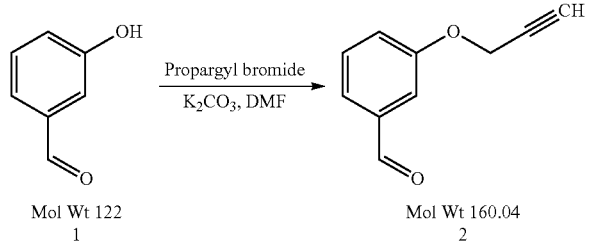

Mol Wt 122
1

Mol Wt 160.04
2

The reaction was carried out in a 6 L reactor, with overhead stirring.

The reactor was charged with 3-hydroxybenzaldehyde (1) (500 g, 4.09M) and the external temperature set to 50° C. DMF (2 L) was added, and the solution stirred. Potassium Carbonate (848 g, 6.14M) was added in portions monitoring for any possible exotherm. ($T_{max}$ 57° C.), the solution turning bright yellow. Propargyl bromide (550 ml, 80 wt % in toluene) was added dropwise over 1.5 hours. A mild exotherm was observed ($T_{max}$ 57° C.).

When the addition was complete, the temperature was increased to 60° C. for 1 hr, the reaction turning to a light brown suspension. After cooling to 25° C., water was added (5 L), and the product extracted with toluene (3 L). The organic phase was washed with water (2×2 L) to remove residual DMF. After separation, the solvent removed in vacuo to give an orange oil which was used without further purification.

The distilled product gradually crystallises on standing (mpt <35° C.).

2) Reduction with Sodium Borohydride

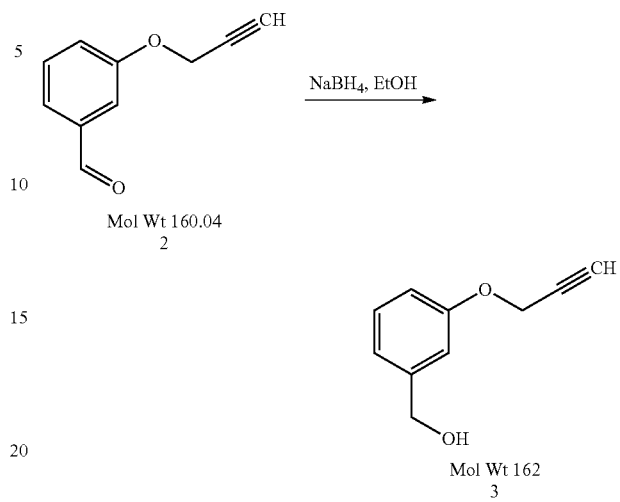

Mol Wt 160.04
2

Mol Wt 162
3

The reaction was carried out in a 6 L reactor, with overhead stirring.

The reactor was cooled to −5° C., and compound (2) was added in 1 L of ethanol then made up to 3 L with ethanol. Sodium borohydride (50 g) was added in approx. 4 g portions, ($T_{max}$ 35° C.) with good stirring. After 30 mins more tlc analysis indicated all starting material has been consumed. The ethanol was removed in vacuo and the residual orange oil dissolved in water (3 L). 140 ml conc HCl was added slowly with stirring. The aqueous layer was extracted with 2×1.5 L of dichloromethane, which was dried over $MgSO_4$, and used in the next step without any further purification.

3) Reaction with Acetyl Chloride

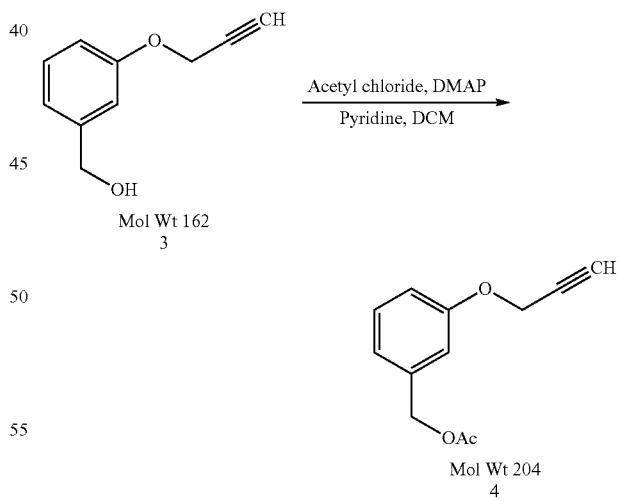

Mol Wt 162
3

Mol Wt 204
4

The reaction was carried out in a 6 L reactor with overhead stirring.

The reactor was charged with the solution of (3) (4.09 moles) in DCM (3 L) from the previous step and cooled to 5° C. Pyridine (500 ml) and DMAP (1 g) was added. Acetyl chloride (365 ml) was then added dropwise so that the internal temperature did not rise above 40° C. When the addition was complete, the reaction was allowed to stir at room temperature for 1.5 hours. Aqueous hydrochloric acid (2N), (200 ml) was added, the reaction stirred and phases separated. The organic layer was washed with 1 L of aqueous potassium carbonate (10 wt %) then with 1 L of brine. The organic extracts were dried over $MgSO_4$, and the solvent removed in vacuo to give and orange oil.

The reaction was repeated 3 times and the products combined. The oil was purified by distillation in portions (0.5 mm Hg, 130° C.) to give (4) as a pale yellow oil (2.4 kg).

Preparation of 3-(o-closo-carboranylmethoxy)benzyl acetate 5

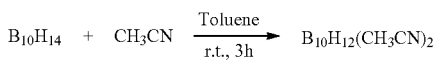

In this reaction step, the decaborane starting material is first reacted with acetonitrile to give the $B_{10}H_{12}(CH_3CN)_2$ reactive intermediate.

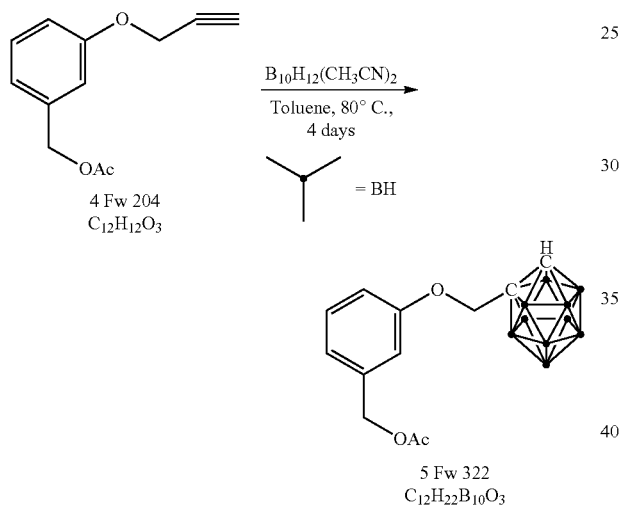

The second stage of this step involves reaction of the activated borane with the alkyne functionality of 4 to give the desired o-closo-carborane subunit.

A 10.0 L flange flask was charged with decaborane ($B_{10}H_{14}$, ex. Katchem, 150 g, 1.23 mol, 1 eq), and anhydrous toluene (4.5 L) to give a clear colourless solution. Acetonitrile (ex. Aldrich, anhydrous, 150 ml) was added and the resulting mixture stirred at room temperature for 3-4 h under nitrogen. The reaction was monitored for hydrogen evolution before proceeding. After hydrogen had stopped evolving, freshly distilled 3-propargyloxybenzyl acetate 4 (251 g, 1.23 mol, 1 eq) was added, and the resulting solution stirred at 80° C. for 3-4 days; the reaction solution becoming slightly yellow. TLC-examination at this time (silica, DCM, PMA or UV developing) showed that almost all of the alkyne 4 had been consumed. The mixture was cooled to room temperature and 2.61 L of a mixture of concentrated HCl (26 ml), water (500 ml), acetone (515 ml) and methanol (1575 ml) were slowly added with aid of an ice/water bath for controlling the possible exotherm, and the resulting two-phase system stirred at room temperature for 16 h to completely destroy any excess decaborane reagent. The toluene layer was separated, the aqueous layer further extracted with toluene (500 ml) and the combined organics evaporated to dryness by rotary evaporation at 40° C./40 mmHg. Removal of the solvent under reduced pressure gave the crude product 5 (307.0 g, 77%), which was used for the next step without further purification.

Preparation of 3-(o-closo-carboranylmethoxy)benzyl alcohol 6

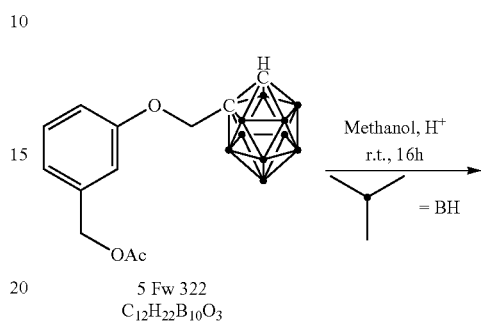

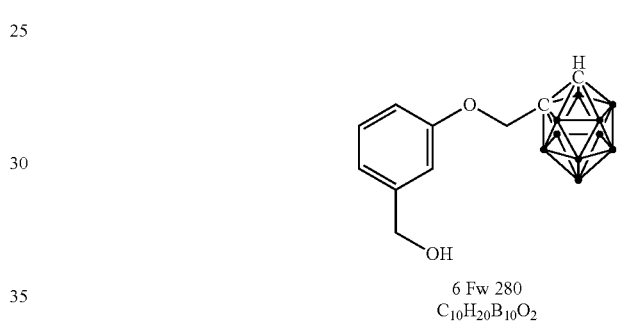

This reaction step was again quite straightforward. The o-closo-carboranylmethoxyl groups in the starting material 5 and the product 6 were stable to the acidic reaction conditions.

Concentrated hydrochloric acid (50.0 ml) was added dropwise, with stirring, to an ice-cold solution of acetate 5 (307.0 g, 0.953 mol, 1 eq) in methanol (3.5 L), and the resulting orange solution was stirred at room temperature for 24 h until TLC-examination (Silica, DCM, UV or PMA develop) showed that all of the string material 5 had been consumed. The solvent was removed by rotary evaporation at 40° C./40 mmHg, and the residue purified by column chromatography on silica gel (1.7 Kg silica, 1:1 DCM/isohexane eluent) to give the alcohol 6 (205.2 g, 77% yield).

An alternative process to compound 6 is outlined below:

4) Introduction of Boron Cage

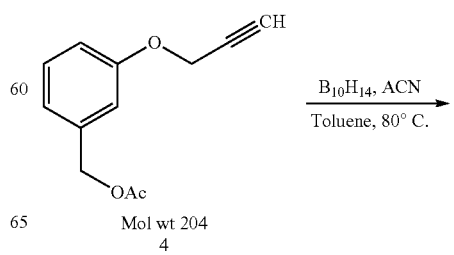

-continued

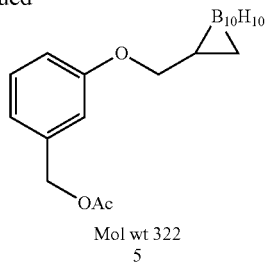

Mol wt 322

5

[NB: All solvents used in this step were first dried by standing over molecular sieves]

A 5 L 3 necked flask was charged with 1.7 L of toluene, and flushed with Nitrogen. Decaborane (200 g) was added under a nitrogen atmosphere. Acetonitrile (200 ml) was added to the reaction and it was heated over 40 mins to approximately 80° C. and maintained at this temperature for 1 hour. Hydrogen evolution was observed, as was the formation of a solid (probably the decaborane:acetonitrile complex forming).

The reaction was removed from the heat. The acetate (4) (334.7 g) was dissolved in toluene (200 ml), and half of the solution added to the stirring decaborane complex. Stirring was continued as the solid was allowed to dissolve. After an initial cooling to 76° C., an exotherm to 81° C. was observed. The rest of the acetate solution was added and heating resumed. 100 ml toluene was used to wash residual acetate into the reaction vessel. Heating was continued for 43 h after which time no starting material remained. The reaction was allowed to cool and the solvent removed in vacuo to give the crude product as an orange oil (655 g).

This was used directly in the next reaction.

5) Removal of the Acetyl Group

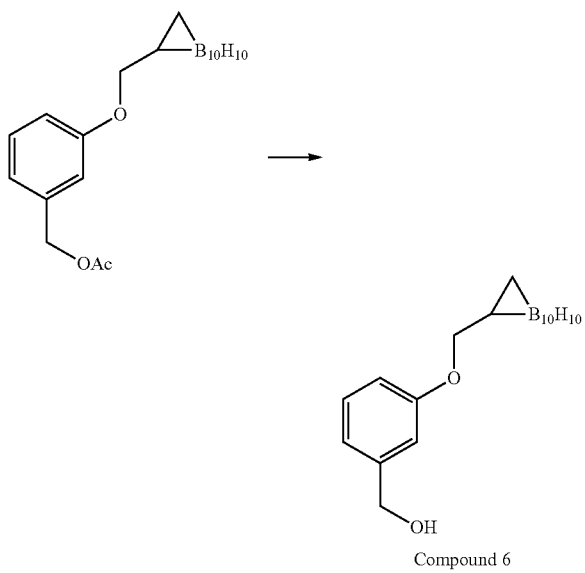

Compound 6

The crude product from the previous stage was dissolved in 2.5 L of methanol and stirred at room temperature (25° C.), monitoring the evolution of hydrogen gas. When no further gas evolution was seen (2-3 h) the reaction was cooled in an ice bath and conc. HCl (65 ml) was carefully added. A temperature increase to 30° C. was observed. After 4 hours the reaction was shown to be almost complete by tlc. Stirring was continued overnight.

After 24 hours the methanol was removed in vacuo at 30° C. When approximately 2 L of methanol had been removed, toluene (1 L) was added and the residual methanol removed. The solution was filtered through silica and the silica washed with dichloromethane until all the product was isolated (tlc analysis).

Solvent was removed and the crude material purified by chromatography using dichloromethane as solvent. Yield of purified product, 204 g plus approximately 50 g mixed fractions which chromatographed with other mixed material.

Compound 6 can also be prepared by the process outlined below. The process allows a more direct synthesis of the compounds of the invention. This process involves the direct addition of the borane cage onto an aldehyde as illustrated below.

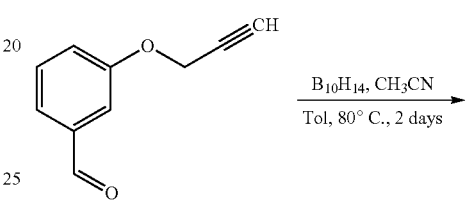

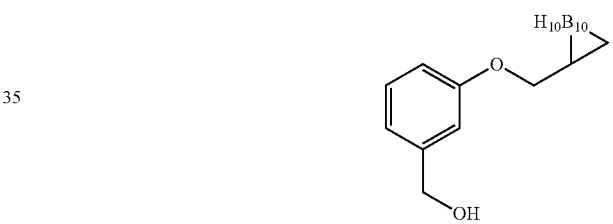

Decaborane (50 g) is dissolved in toluene (450 ml) under nitrogen. Acetonitrile (50 ml) is added and the mixture heated at 80° C. for 3 h. The aldehyde (64 g) in toluene (50 ml) is added and the mixture heated for 40 h (no starting material). The solvent is removed under vacuum and the residue heated at reflux in methanol for 8 h to destroy borane residues. Solvent is removed and the product isolated by chromatography using dichloromethane as solvent.

Fraction 1 9.3 g, contaminated with higher $R_f$ borane residues

Fraction 2 56.7 g, main fraction

Fraction 3 2.3 g, contaminated with lower $R_f$ borane residues

The product is shown to be identical by HPLC to the product generated by alternative procedures.

Decaborane (2.25 g) is heated at reflux in 15 ml HPLC grade acetonitrile for 3 h (suspended solid). Compound 4 (3.7 g) in acetonitrile (10 ml) is added. The mixture is heated for 8 h (complete consumption of starting material), cooled, and the solvent removed. The residue is dissolved in dichloromethane and filtered through silica, washing with about 100 ml dichloromethane. The solvent is removed to give 4.2 g of the crude product.

The use of acetonitrile has resulted in an acceleration of the reaction between decaborane and compound 4. This acceleration was unexpected and provides a significant benefit and advancement in the production of compounds of the invention.

Preparation of 3-(o-closo-carboranylmethoxy)benzaldehyde 7

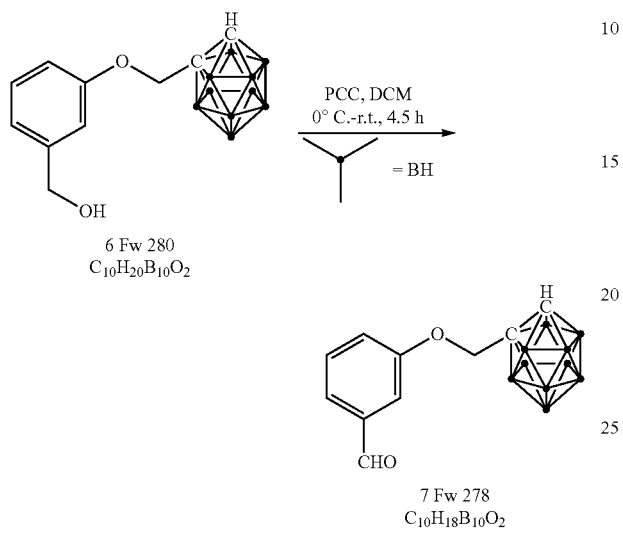

This was a relatively routine step, and the yield of the product aldehyde 7 was quite high (90%). A significant factor in this step was that it was necessary to carry out the oxidation under strictly anhydrous conditions or else it failed.

A solution of alcohol 6 (205.0 g, 0.732 mol, 1 eq) in dry DCM (1.5 L) was added dropwise to an ice-cooled suspension of pyridinium chlorochromate (PCC, 244.6 g, 1.135 mol, 1.55 eq) in dry DCM (750 ml), and the resulting mixture sired at room temperature for 4.5 h. TLC-examination showed (silica, DCM, UV or PMA develop) that all of the alcohol 6 had been consumed. The mixture was filtered through a pad of silica gel (1.5 kg of silica), and the filter cake was washed with DCM. The filtrate was then evaporated to dryness to give the product 7 (187 g, 92% yield) as a colourless solid.

An alternative and higher yielding synthesis of compound 7, which avoids the need for oxidation, is outlined below:
Step A Decaborane (12.2 g, 0.1 mole) is heated at reflux in 50 ml acetonitrile for 5 h. The volume of solvent is reduced to about 50% and replaced with 75 ml dry toluene. Propargyl acetate (19.8 g, 0.2 mole) is added and the mixture heated at 80-90° C. for 36 h. Solvents and excess reagent are removed by rotary evaporation. The residue is dissolved in 50 ml methanol and 5 ml conc. HCl is added. After leaving overnight, the solvent is reduced to low volume, toluene (100 ml) added and the toluene solution washed with 10% potassium carbonate. After removal of the solvent, the residue is dissolved in a small volume of dichloromethane and passed through a short plug of silica, eluting with dichloromethane. After removal of the solvent, 12.9 g product is obtained.

The alcohol is dissolved in dichloromethane (60 ml). Pyridine (12 ml, 2 eq) is added and the mixture cooled to 0-5° C. Methanesulphonyl chloride (7.1 ml, 1.25 eq) is added and the mixture stirred for 5 hours then 1 h at room temperature. The reaction is quenched with 100 ml 2M HCl, the layers separated and the organic layer washed with water and dried. After removal of the solvent, the crude residue is treated with 3-hydroxybenzaldehyde (12.2 g, 1.3 eq), potassium carbonate (20 g) in DMF (60 ml) at 90-100° C. for 8 h. The mixture is poured onto water (250 ml) and extracted with toluene (100 ml then 50 ml). The combined toluene extracts are washed with 50 ml 10% potassium carbonate solution then water and dried. Evaporation of the solvent affords compound 7 (18.9 g). The compound can be purified further by recrystallisation from diisopropyl ether if required.

Preparation of (α,β,γ,δ-tetra-[3-(1,2-dicarbododecaborane (12)-1-ylmethoxyl)-phenyl]porphyrin 8

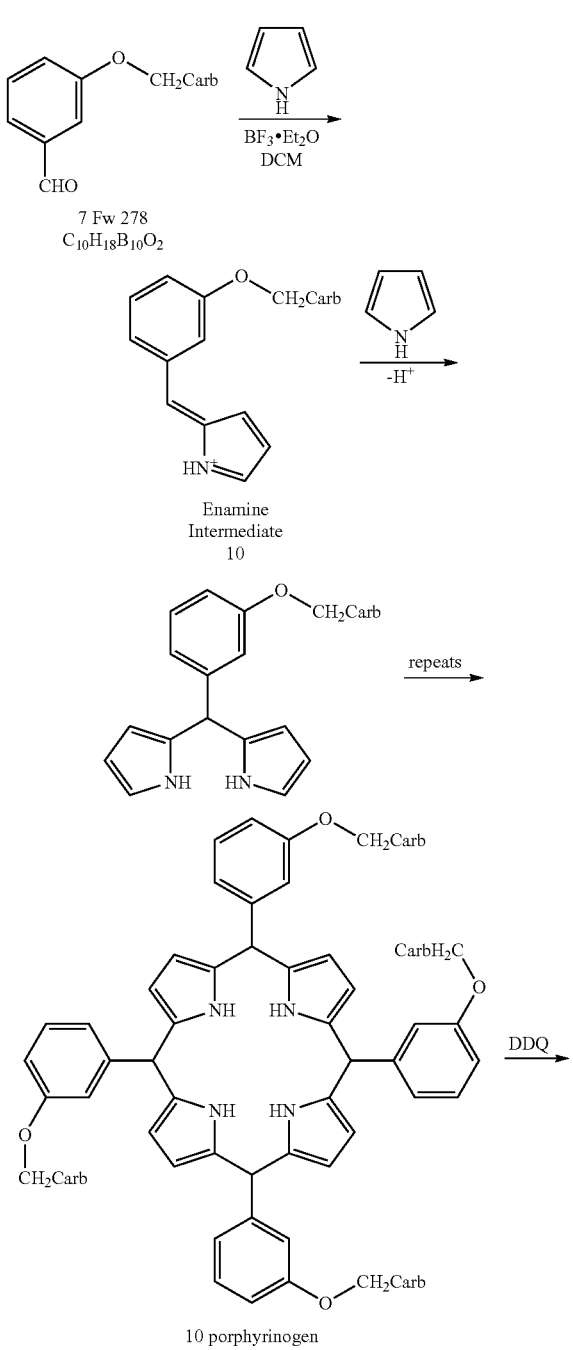

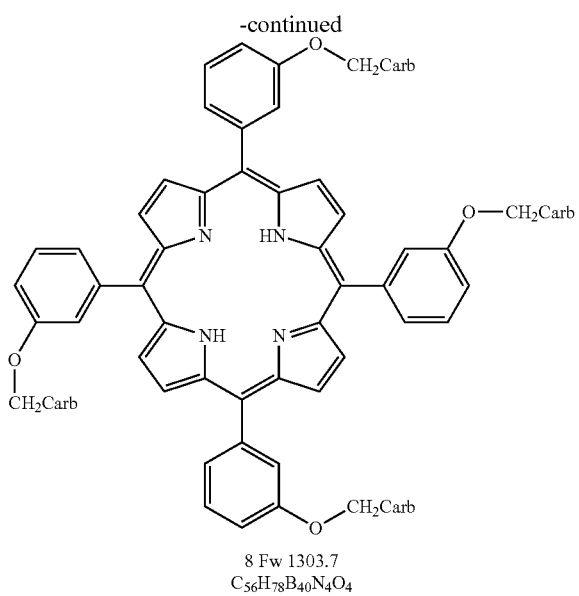

8 Fw 1303.7
$C_{56}H_{78}B_{40}N_4O_4$

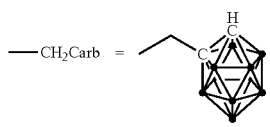

A 10 L flange flask equipped with an overhead stirrer and a nitrogen inlet/outlet, was charged with aldehyde 7 (163 g, 0.586 mol. 1 eq), dry DCM (8.0 L) and freshly distilled pyrrole (39.26 g, 0.586 mol, 1 eq) and a stream of dry nitrogen bubbled through the reaction mixture for 24 min to remove all traces of oxygen. Boron trifluoride diethyl etherate (3.52 ml) was added, and the resulting solution stirred at room temperature for 1.5 h, taking on a red/brown colouration. TLC (silica, 1:1 DCM/isohexane) showed that all 7 had been consumed. Activated 4 Å molecular sieves (106 g) were added to remove all traces of water and the resulting solution stirred for 30 min. The reaction mixture was then treated with 2,3-dichloro-5,6-dicyanobenzo-quinone (DDQ, 101 g, 0.44 mol, 0.76 eq) and stirred at room temperature for 20 h. The reaction mixture was filtered to remove the sieves and the product was loaded onto a silica-gel column (1.0 Kg silica, 1:1 DCM/isohexane to 100% DCM gradient). As the elution was carried out the crude material precipitated out on the column and so it was necessary to extract/wash the product off the silica gel using methanol (6×10.0 L). The product was isolated by filtering and concentrating the methanolic extracts/washes, which gave 60.9 g (32% yield) of the slightly impure porphyrin 8. This material was combined with the product from a pilot reaction to give 71.4 g of the porphyrin 8.

Preparation of α,β,γ,δ-tetra-[3-(1,2-dicarbododecaborane (12)-1-ylmethoxyl]phenyl-porphorynato-copper(II) 9

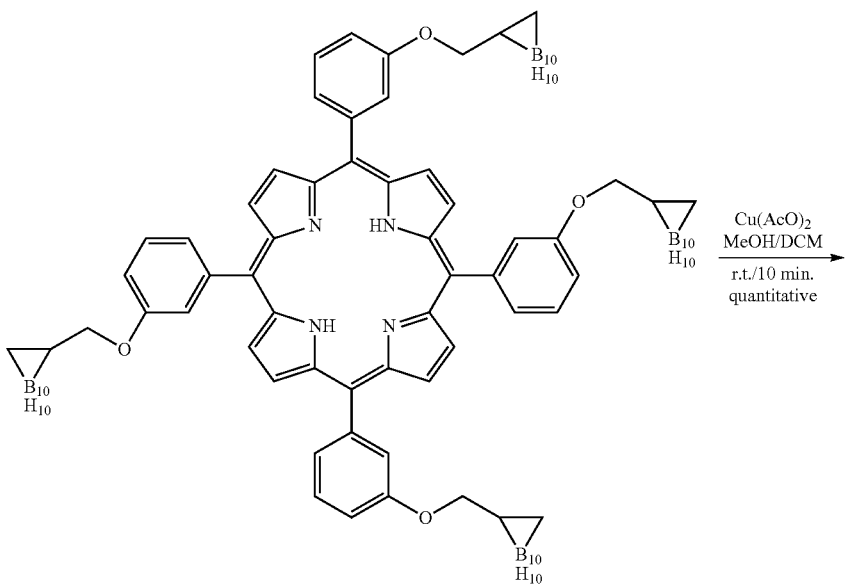

8 Fw 1303
$C_{56}H_{78}B_{40}N_4O_4$

-continued

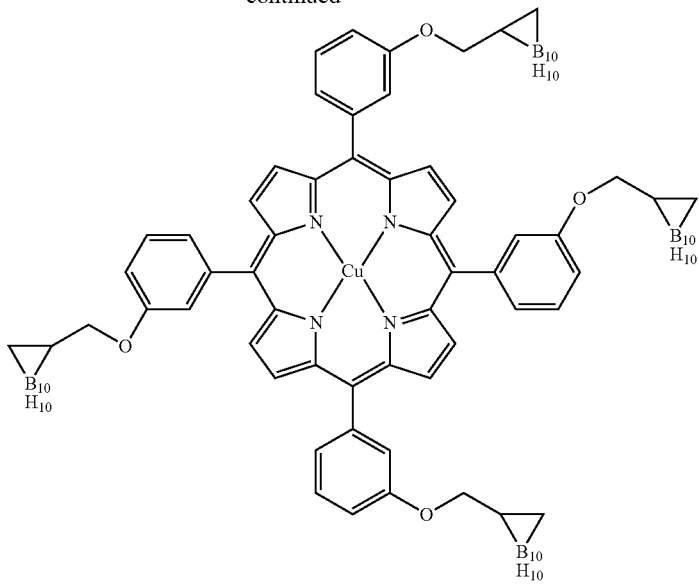

9 Fw 1365
$C_{56}H_{76}B_{40}N_4O_4Cu$

The cupration reaction proceeded smoothly at room temperature in a DCM and methanol mixed solvent system in almost quantitative yield.

Copper(II) acetate (55.6 g) was mixed with dry methanol (5.54 L) and the mixture heated to 50° C. for 20 h, resulting in a clear, blue-coloured solution, which was cooled to room temperature then added to a stirred, dark purple coloured, solution of porphyrin 8 (71.4 g, 54.79 mmol) in DCM (2.79 L). The reaction mixture was stirred at room temperature for 10 min, taking on a dark red colouration, after which TLC (silica, 1:1 DCM/isohexane) showed complete consumption of 8. The dark red solution was concentrated to half volume on a rotary evaporator at 30° C./40 mmHg, then diluted with DCM (2.0 L). The resulting solution was passed through a pad of silica-gel (2×1.5 kg), which was washed with DCM to give a solution of 9. The solvents were evaporated to give 64.6 g (86% yield) of 9.

Preparation of 1,2,3,4,5,6,7,8-octabromo-α,β,γ,δ-tetra-[3-(1,2-dicarbododecaborane (12)-1-yl-methoxyl)phenyl]porphynato-copper(II)

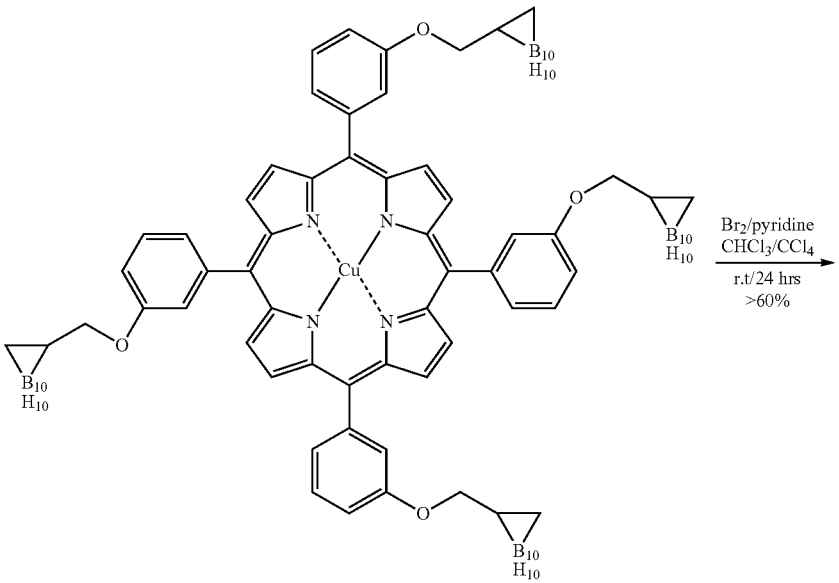

9 Fw 1365
$C_{56}H_{76}B_{40}N_4O_4Cu$

-continued

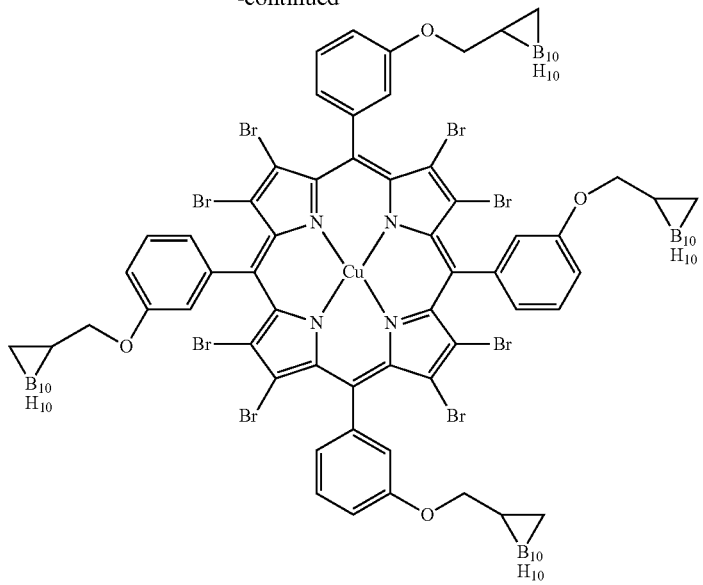

Fw 1996
C56H68B40Br8N4O4Cu

A solution of bromine (229 g, 73.5 ml, 1.43 mol) in a mixture of carbon tetrachloride and dry chloroform (1.2 L each) was added dropwise, at room temperature, over 1 h to a stirred solution of porphyrin 9 (64.6 g, 47.32 mmol) in chloroform/CCl$_4$ (6.0 L each) and the resulting solution stirred for 4 h. Pyridine (193 ml, 188.5 g, 2.38 mol) was added and the resulting mixture stirred at room temperature for a further 20 h. TLC (silica, 1:1 DCM/isohexane) showed that all of the starting material had been consumed. A 20% aqueous solution of Na$_2$S$_2$O$_5$ (2.7 L) was then added, and the mixture stirred vigorously for ~10 min to destroy any excess bromine. The mixture was diluted with water (2.7 L), the stirring continued for 10 min, and the organic and aqueous phases separated. The organic phase was washed with water (2.7 L), dried over sodium sulfate, filtered, and the solvents evaporated at 30° C./40 mmHg to give a dark coloured residue. This was purified by passing through a pad of silica (1.3 Kg) (1:1 DCM/isohexane eluent) to give 10 (71 g, 75%) as a very dark green solid. Mass spectrum (MALDI-TOF LD$^+$ in dithranol) analysis showed the expected molecular ion pattern.

Production of a Compound of Formula I Using the One-Pot Procedure

The following example is provided as a non-limiting example of the above procedure:

Finely powdered copper acetate, 130 mg (1.4 equivalents) and (α,β,λ,δ-tetra-[3-(1,2-dicarbododecaborane (12)-1-yl-methoxyl)phenyl]porphyrin, 0.65 g (0.5 mmole) are rapidly stirred in dichloromethane (23 ml) for approximately 2 hours, or until complete by HPLC analysis. To this is added 3.6 ml of a freshly prepared 10% solution of bromine in HPLC grade methanol (14 eq) with the temperature at about 20° C. The mixture gradually darkens as PP 200 forms. After about 8 h, the reaction is shown to be complete by HPLC analysis. Sodium bicarbonate (2.5 g) is added and the mixture stirred for 10 minutes. The mixture is filtered through a pad of celite, which is washed with dichloromethane (50 ml).

The solvents plus excess bromine are removed, keeping the temperature below 30° C. The residue is dissolved in a minimum volume of dichloromethane and purified by passing through a pad of silica eluting with dichloromethane. After removal of solvent and high vacuum treatment, 0.95 grams of product is obtained which is of a similar purity to previously described procedures.

The invention claimed is:

1. A process for the production of a compound of formula I

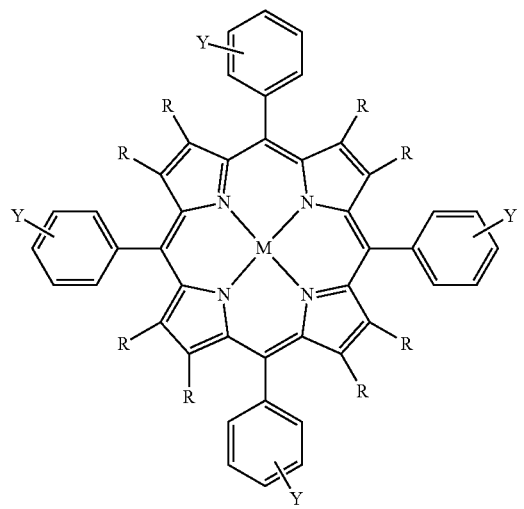

wherein M is a single-photon-emission tomography imageable radiometal and/or a paramagnetic metal, R is hydrogen or a halogen provided that at least one R is halogen and Y is selected from ortho, meta or para O(CH$_2$)$_n$C$_2$HB$_9$H$_{10}$ or O(CH$_2$)$_n$C$_2$HB$_{10}$H$_{10}$ wherein n is 0 or an integer from 1 to 20 and O(CH$_2$)$_n$C$_2$HB$_9$H$_{10}$ is nido ortho-, meta- or para-carborane and O(CH$_2$)$_n$C$_2$HB$_{10}$H$_{10}$ is ortho-, meta- or para-carborane, said process comprising the in situ generation of a compound of formula III

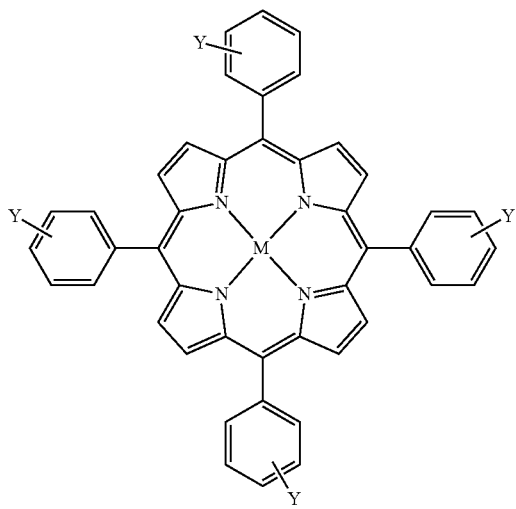

according to a process comprising:
a) combining a compound having the formula II

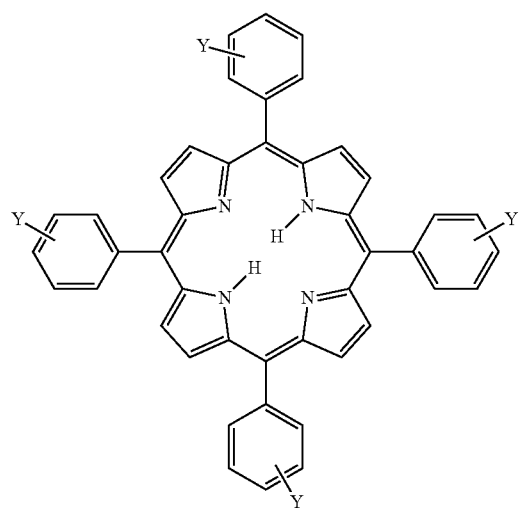

with the acetate of M, to form a compound having the formula III in situ, and
b) combining the in situ generated compound of formula III with a halogenating agent bromine in methanol to form a compound having the formula I.

2. A process according to claim 1 wherein M is Cu.

3. A process according to claim 1 wherein the compound having the formula III is combined with 8 to 20 equivalents of the halogenating agent.

4. A according to claim 1 wherein the compound having the formula II is combined with the acetate of M in dichloromethane or in a mixture of dichloromethane and methanol.

5. A process according to claim 1 wherein the compound having the formula II is combined with 1 to 5 equivalents of the acetate of M.

6. A process according to claim 1 wherein M is Cu, each R is bromide and Y is meta $O\text{---}CH_2\text{---}C_2HB_{10}H_{10}$.

7. The process of claim 1, wherein the compound of formula II is prepared by a process comprising:
combining an aldehyde having the formula

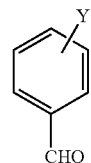

with pyrrole in the presence of a Lewis acid catalyst to form a compound having the formula IV

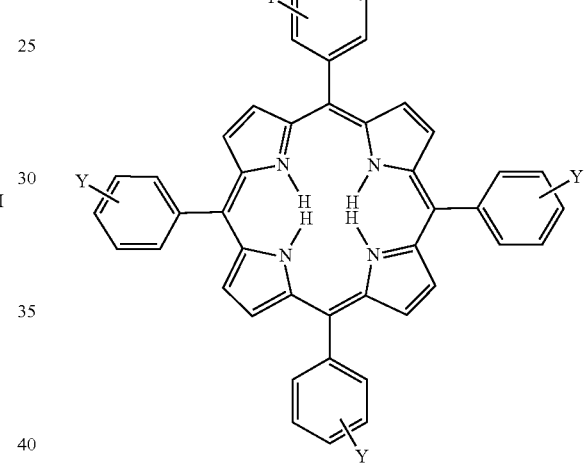

and oxidising the compound having the formula IV by the addition of from 0.1 to 2 molar equivalents 2,3-dichloro-5,6-dicyanobenzoquinone based on the aldehyde to form a compound having the formula II.

8. A process according to claim 7 wherein the pyrrole is at least 98% to 99.99% pure and optionally freshly distilled.

9. A process according to claim 7 further comprising a step of removing all traces of water prior to the oxidation of the compound of formula IV.

10. A process according to claim 7 wherein the step of combining a compound of formula II with the acetate of M is carried out in dichloromethane.

11. A process according to claim 7, wherein the aldehyde is prepared by a process comprising activation of a carborane with acetonitrile, reaction with propargyl oxybenzyl acetate to form an alcohol and subsequent oxidation.

12. A process according to claim 7 wherein the step of combining the compound having formula III with bromine is carried out at ambient temperature.

13. A process according to claim 7 wherein M is Cu, each R is bromide and Y is meta $O\text{---}CH_2\text{---}C_2HB_{10}H_{10}$.

* * * * *

UNITED STATES PATENT AND TRADEMARK OFFICE
CERTIFICATE OF CORRECTION

PATENT NO. : 8,680,265 B2  Page 1 of 1
APPLICATION NO. : 11/721865
DATED : March 25, 2014
INVENTOR(S) : Bury et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1707 days.

Signed and Sealed this
Twenty-ninth Day of September, 2015

Michelle K. Lee
*Director of the United States Patent and Trademark Office*